United States Patent [19]

Movern

[11] Patent Number: 5,183,466
[45] Date of Patent: Feb. 2, 1993

[54] RESTRICTED USE HYPODERMIC SYRINGE
[76] Inventor: John B. Movern, 3622 Norton Place, NW., Washington, D.C.
[21] Appl. No.: 708,978
[22] Filed: Jun. 3, 1991

Related U.S. Application Data

[62] Division of Ser. No. 400,060, Aug. 29, 1989, Pat. No. 5,021,047.
[51] Int. Cl.⁵ ............................................. A61M 5/00
[52] U.S. Cl. ................................. 604/110; 604/218
[58] Field of Search .............. 604/110, 187, 208, 209, 604/210, 218, 220

[56] References Cited

U.S. PATENT DOCUMENTS

| | | | |
|---|---|---|---|
| 4,731,068 | 3/1988 | Hesse | 604/110 |
| 4,820,272 | 4/1989 | Palmer | 604/110 |
| 4,826,483 | 5/1989 | Molnar, IV | 604/210 X |
| 4,887,999 | 12/1989 | Alles | 604/208 X |

FOREIGN PATENT DOCUMENTS

| | | | |
|---|---|---|---|
| 0178023 | 4/1986 | European Pat. Off. | |
| 307220 | 12/1968 | Sweden | |
| 8900432 | 1/1989 | World Int. Prop. O. | 604/110 |

Primary Examiner—John D. Yasko
Attorney, Agent, or Firm—Frederick R. Handren

[57] ABSTRACT

A restricted use hypodermic syringe employs a plunger assembly which enables it to be filled and used conventionally but not reused. The plunger assembly incorporates a plunger lock positioned in the syringe barrel about the plunger rod. The plunger lock engages the inner wall of the barrel to form a one-way brake which allows movement of the plunger lock forwardly in the barrel but prevents its rearward movement. The plunger lock also engages the plunger rod to form a one-way clutch which allows the plunger rod to move rearwardly relative to the plunger lock and couples the plunger rod and plunger lock for movement together in the forward direction. The syringe is provided to the user with the piston of the plunger assembly positioned forwardly and the plunger lock positioned rearwardly in the syringe barrel. The syringe is filled by withdrawing the piston. Subsequent forward movement of the piston to expell liquid shifts the plunger lock forwardly in the barrel to a position which prevents or limits a subsequent withdrawal of the piston.

16 Claims, 6 Drawing Sheets

RESTRICTED USE HYPODERMIC SYRINGE

This application is a division of application Ser. No. 07/400,060 now U.S. Pat. No. 5,021,047 filed Aug. 29, 1989.

BACKGROUND OF THE INVENTION

1. Field of the Invention

The present invention relates to a hypodermic syringe which is used for administering liquids such as medicaments to humans and other animals. Specifically, the inventive syringe here disclosed and claimed incorporates features which enable it to be filled and used conventionally and then rendered unfit for further use.

Recently the spread of diseases, especially the deadly disease known as AIDS, through the sharing of contaminated hypodermic syringes has received widespread public attention. It is now well known, for example, that hypodermic syringes used for administering illegal drugs frequently are used repetitively and by different persons with the consequent transmission of disease after the syringe needle becomes contaminated. A syringe that would not lend itself to repeated use would thus be helpful in combatting the spread of disease as well as the use of illegal drugs.

2. Description of Prior Art

Some hypodermic syringes, such as those which are prefilled with medicament, employ a coupling between the piston and the plunger rod which will break when pulling force is applied to the plunger rod. Such syringes cannot be refilled and are thus unfit for repeated use. However, an attendant disadvantage of syringes with a break away piston/plunger rod coupling is that they cannot be filled by the user from a sealed vial, and many liquid medicaments are available only in sealed vials.

Hypodermic syringes which can be filled and used conventionally and then rendered unfit for further use are disclosed in U.S. Pat. No. 4,731,068 issued to John E. Hesse. These syringes, however, are quite complex, with attendant high production costs and increased likelihood of a malfunction which would allow the syringe to be reused.

OBJECTS OF THE INVENTION AND SUMMARY

An object of the present invention is provide a hypodermic syringe that can be properly used once and is then unfit for further use.

Another object of the present invention is to provide a hypodermic syringe which, while preventing repeated use, can be filled and used conventionally.

Another object of the present invention is to provide a hypdermic syringe of simple and economical construction which reliably allows its legitimate use while preventing reuse.

The foregoing objects of the invention, and others as well, are realized by the syringe of the present invention which employs a plunger assembly incorporating a plunger lock which allows withdrawal of the piston for filling with a fluid and which then moves forwardly in the syringe barrel as the piston is advanced to discharge the fluid. A one-way brake formed between the plunger lock and the barrel and a one-way clutch formed between the plunger lock and the plunger rod blocks subsequent withdrawal of the piston beyond the forward position to which the plunger lock moved during the preceding advancement of the piston.

The detailed description provided below together with the accompanying drawings will afford a further understanding of the present invention. Specific embodiments which are disclosed should be regarded as illustrative and not restrictive of the scope of the invention, since obvious modifications of these embodiments will occur to persons of ordinary skill in the art having the benefit of this disclosure.

DESCRIPTION OF PREFERRED EMBODIMENTS

FIGS. 1-5 show the construction and operation of an embodiment of the restricted use syringe which is illustrative of the inventive concept.

Figures 1, 1A, 2:
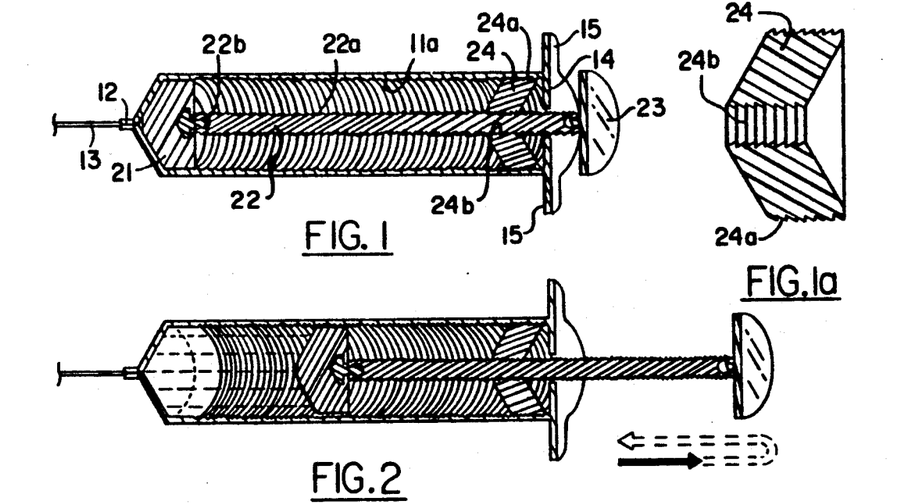
FIG. 1 shows an embodiment of the syringe of the present invention.
FIG. 1a shows, in enlarged detail, a plunger lock used in the syringe of FIG. 1.
FIG. 2-5 show an operating sequence for the syringe of FIG. 1.

As shown in FIG. 1 in its condition prior to loading, the syringe 10 comprises a tubular barrel 11 which is most easily formed with a circular cross-sectional shape, but other shapes, oval, for one, could obviously be used if desired. The barrel is provided at the forward end thereof with means in the form of a fitting 12 for mounting a hypodermic needle 13. As is conventional, within the fitting 12 is a fluid passage providing communication between a fluid passage in the needle and the interior of the barrel 11. At the rear open end of the barrel are an inwardly extending lip 14 and finger-gripping flanges 15 which, for illustration only, are shown as integral with the barrel. Obviously, the lip and the flanges could be formed on a separately applied end cap. Coaxially received in the barrel is a plunger assembly which includes a piston 21, a plunger rod 22 and a plunger lock 24. The piston is formed of a yieldable material such as rubber and sized to sealingly engage the inner wall surface of the barrel. The piston is joined to the forward end of a plunger rod 22 which extends through the opening at the rear end of the barrel. At its rear end, the plunger rod is provided with an actuating flange 23. As illustrated, the joints 22b and 22c between the plunger rod and piston and between the plunger rod and actuating flange preferably are of a snap-together type, such as a resilient ball-and-socket joint, and either of these joints will separate if a sufficient pulling force is applied to them. A plunger lock 24 is positioned within the barrel between the plunger rod and the barrel inner sidewall. As best shown in FIG. 1a, the plunger lock is in the form of an annular stopper with outwardly and rearwardly angled front and rear faces and an outer peripheral surface formed with rearwardly raked teeth 24a and a central opening defined by a surface with rearwardly raked teeth 24b. The teeth 24a engage annular corrugations 11a formed on the inner surface of the barrel. These corrugations may be in the form of annular ridges, which may be forwardly raked, with rounded or pointed peaks. Either or both of the teeth 24a and the corrugations 11a exhibit some resiliency which enables them to form a one-way brake which allows the plunger lock 24 to move forwardly but not rearwardly in the barrel. Obviously, the annular stopper could be made thicker in axial dimension than it appears in FIGS. 1-5 if a stronger brake were desired. The teeth 24b in the central opening of the plunger lock engage forwardly raked teeth 22a formed on the plunger rod.

Either or both of the teeth 24b and 22a are somewhat resilient, and they form a one-way clutch which couples the plunger lock to the plunger rod for forward movement together in the barrel but allows relative rearward movement of the plunger rod within the plunger lock.

Figure 3:
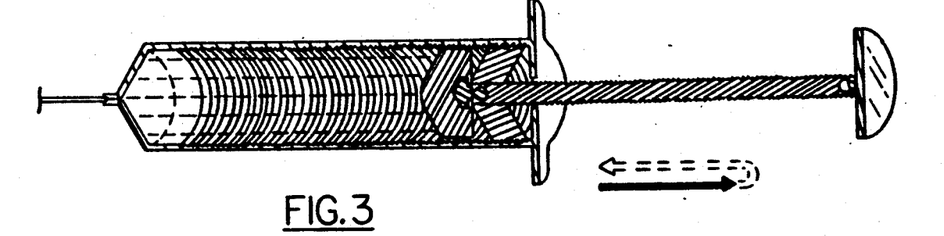
Figure 4:
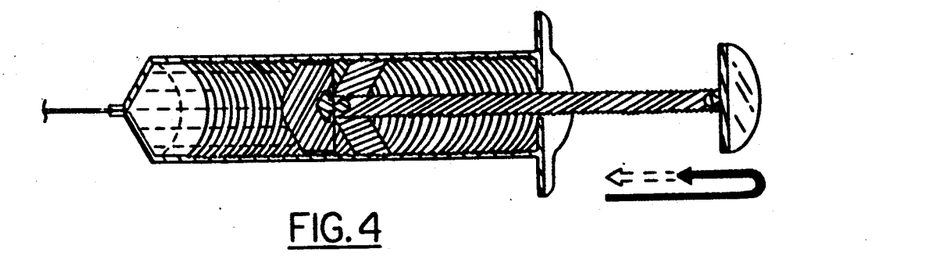
Figure 5:
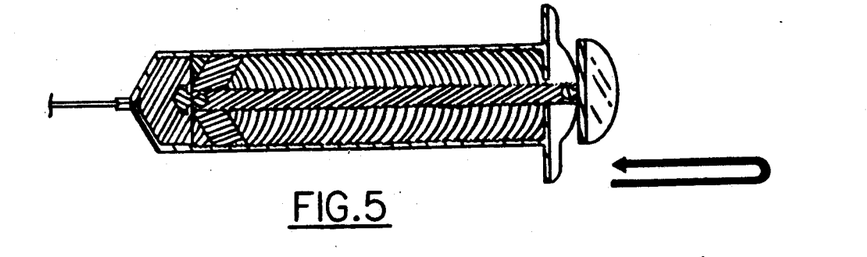

FIGS. 2-5 illustrate an operating sequence for the restricted use syringe, with movement of the plunger indicated by the solid portion of the U-shaped arrow. FIGS. 2 and 3 show respectively the intermediate and fully withdrawn positions of the piston and plunger rod. With the needle inserted into a supply of liquid medicament, the rearward movement of the piston will draw the medicament into the barrel ahead of the piston. During the rearward movement of the piston and plunger rod, the teeth 24b of the plunger lock will ride over the teeth 22a of the plunger rod, and the engagement of the teeth 24a at the periphery of the plunger lock with the corrugations 11a on the inner surface of the barrel will hold the plunger lock against rearward movement. FIGS. 4 and 5 show respectively the intermediate and fully advanced positions of the plunger assembly. As the piston moves forwardly in the barrel it will force the liquid medicament ahead of it through the needle. During the forward movement of the plunger assembly, the engaged teeth 24b and 22a of the plunger lock and the plunger rod will cause the plunger lock to move forwardly in the barrel as the teeth 24a at the periphery of the plunger lock ride over the corrugations 11a formed on the inner surface of the barrel. Once the condition shown in FIG. 5 is reached, subsequent rearward movement of the piston and plunger rod in the barrel will be prevented by the abutment of the piston with the plunger lock which, due to the one-way brake formed between teeth 24a and corrugations 11a, is held against rearward movement. If enough rearward force is applied to the plunger rod, either or both of the joints at the forward and rear ends of the plunger rod will separate. Thus, once the condition shown in FIG. 5 is reached, subsequent attempts to fill the syringe will be thwarted.

Variations on the operating sequence shown in FIGS. 2-5 are possible. For example, if the liquid medicament to be administered were contained in a sealed vial, the piston could be initially withdrawn slightly to draw in air before the needle is inserted in the vial. Alternatively, the syringe could be shipped to the user with the piston slightly displaced from its forwardmost position in the barrel. Then, a forward movement of the piston would force the air into the vial to pressurize it as an aid to transferring the liquid medicament to the syringe during a subsequent rearward movement of the piston. During the air-expelling forward movement of the piston, the plunger lock will be carried forward in the barrel and will establish a new, slightly shorter limit to the medicament-filling rearward movement of the piston. The syringe could, of course be designed to deliver an optimal dose of medicament after the reduction in the piston stroke length.

The syringe could also be used to deliver less than a full volume dose. In this mode of operation, a partial withdrawal of the piston in the barrel for filling followed by a forward movement of the piston to its forwardmost position will shift the plunger lock to an intermediate position in the barrel. If desired, the piston could then be withdrawn to an extent limited by the intermediate position of the plunger lock and then moved fully forwardly to shift the plunger lock to its forwardmost position so as to prevent any subsequent filling of the syringe. Alternatively, the syringe could be shipped to the user with the plunger lock partially advanced in the barrel to thereby limit its volume.

Figures 6, 7, 8, 9, 10, 11, 12, 13, 14:
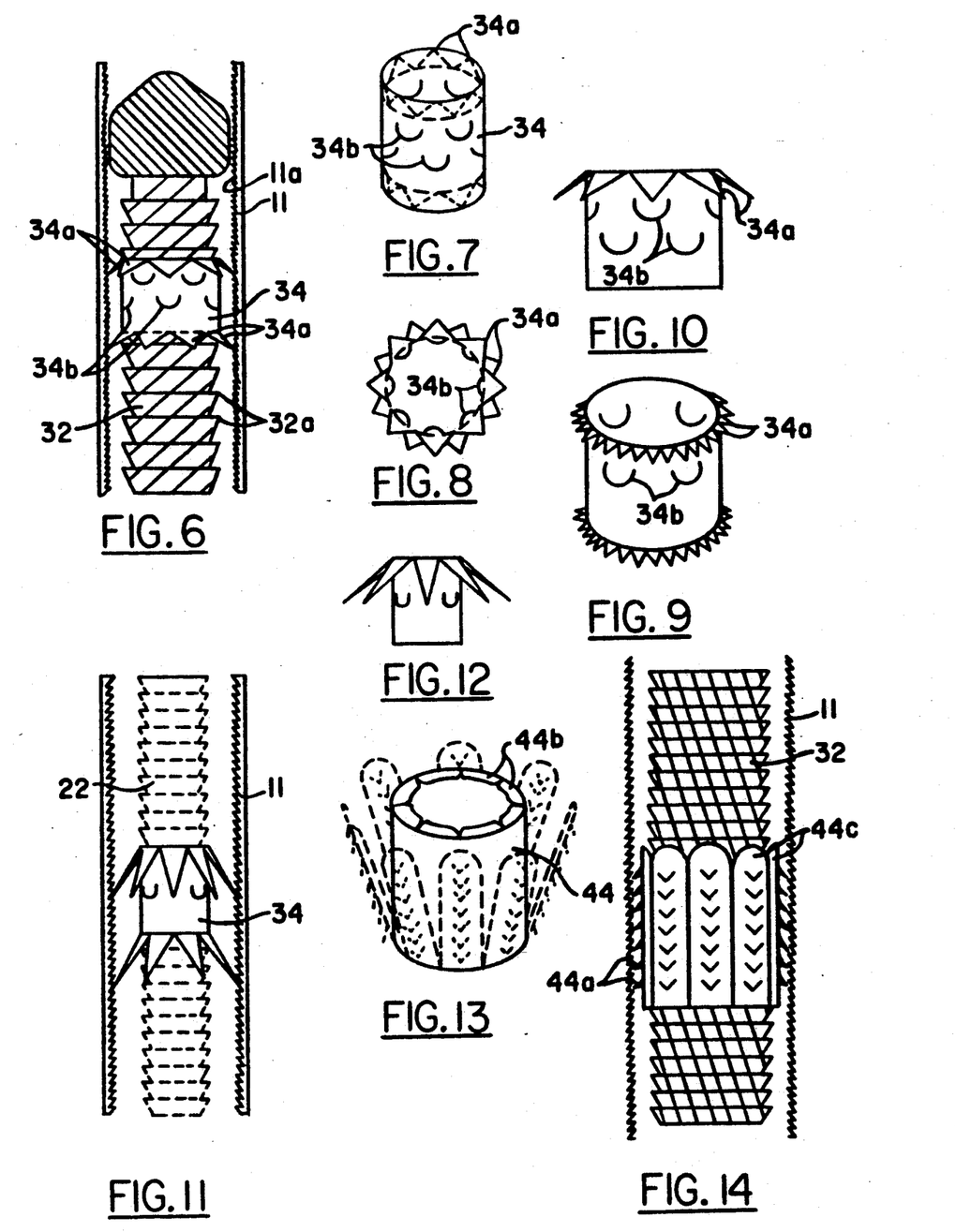
FIG. 6 shows a section of a syringe employing a plunger lock formed from tubing.
FIG. 7 shows the formation of the plunger lock of FIG. 6.
FIG. 8 shows an axial view of the plunger lock of FIG. 6.
FIGS. 9 and 10 show variations on the plunger lock of FIG. 6.
FIG. 11 shows a section of a syringe employing another embodiment of a plunger lock formed from tubing.
FIG. 12 shows a variation on the plunger lock of FIG. 11.
FIG. 13 shows the formation of another plunger lock formed from tubing.
FIG. 14 shows a section of a syringe employing the plunger lock of FIG. 13.

FIGS. 6–8 illustrate another embodiment of the inventive restricted use syringe. As shown in FIG. 7, the plunger lock 34 is formed from tubing, or from a flat strip formed into a tube, with outwardly and rearwardly struck teeth 34a at its leading and trailing ends. As shown in FIG. 6, these teeth engage the inner surface of the syringe barrel to form a one-way brake which allows movement of the plunger lock only toward the forward end of the syringe barrel. The tubular body of the plunger lock is provided with inwardly and forwardly struck tabs 34b which engage the outer surface of the plunger rod 32 to form a one-way clutch which allows movement of the plunger rod relative to the plunger lock only in the rearward direction.

In the embodiment of FIGS. 6–8, the teeth 34a engage corrugations 11a, like those in the embodiment of FIGS. 1–5, formed on the inside surface of the barrel 11. Also, the tabs 34b engage forwardly raked teeth 32a formed on the outer surface of the plunger rod. However, in this embodiment, as in other embodiments of a plunger lock formed from tubing or sheet material, if the material forming the barrel and the plunger rod were soft enough, plastic, for example, and if the material forming the plunger lock were hard enough, metal, for example, the corrugations 11a in the barrel and the forwardly raked teeth on the plunger rod could be eliminated so that the inner surface of the barrel and the outer surface of the plunger rod are smooth. In this modification, the teeth 34a and tabs 34b of the plunger lock would bite into the surfaces of the barrel and plunger rod to provide the one-way brake and one-way clutch.

As shown in FIG. 6, the plunger rod 32 is considerably thicker relative to the inner transverse dimension of the barrel than the plunger rod 22 of the FIGS. 1–5 embodiment so as to provide greater stability to the plunger rod and the plunger lock. In this and the other embodiments, the illustrated size relationship of the parts is only exemplary, and obviously persons of ordinary skill in the art will seek optimum proportions through routine experimentation.

FIGS. 9 and 10 illustrate modifications of the plunger lock embodiment of FIGS. 6–8. The modification shown in FIG. 9 employs a single tier of inwardly struck tabs 34b and a large number of outwardly struck teeth 34a at the leading and trailing ends of the tubular body. The modification shown in FIG. 10 employs outwardly struck teeth 34a only at the leading end of the tubular body.

FIGS. 11 and 12 illustrate other modifications of the plunger lock of FIGS. 6–8. The plunger lock shown in FIG. 11 is proportioned so that it will function on a plunger rod which is slender compared to the plunger rod employed in the embodiment of FIGS. 6–8 The plunger lock shown in FIG. 12, like the one shown in FIG. 10, has outwardly struck teeth 34a only at the leading end of the tubular body.

Another plunger lock formed from tubing is shown in FIGS. 13 and 14. At its leading end, plunger lock 44 is provided with inwardly and rearwardly struck tabs 44b which engage the outer surface of the plunger rod 32 to form a one-way clutch. Several arms 44c are folded forwardly from the trailing end of the plunger lock so as to lie along the tubular body of the plunger lock. Struck from each of the arms are several teeth 44a which, in the folded orientation of the arms, extend outwardly and rearwardly. As shown in FIG. 14, these teeth engage the inner surface of syringe barrel 11 to form a one-way brake.

Figures 15, 16, 17, 18, 19, 20, 21:
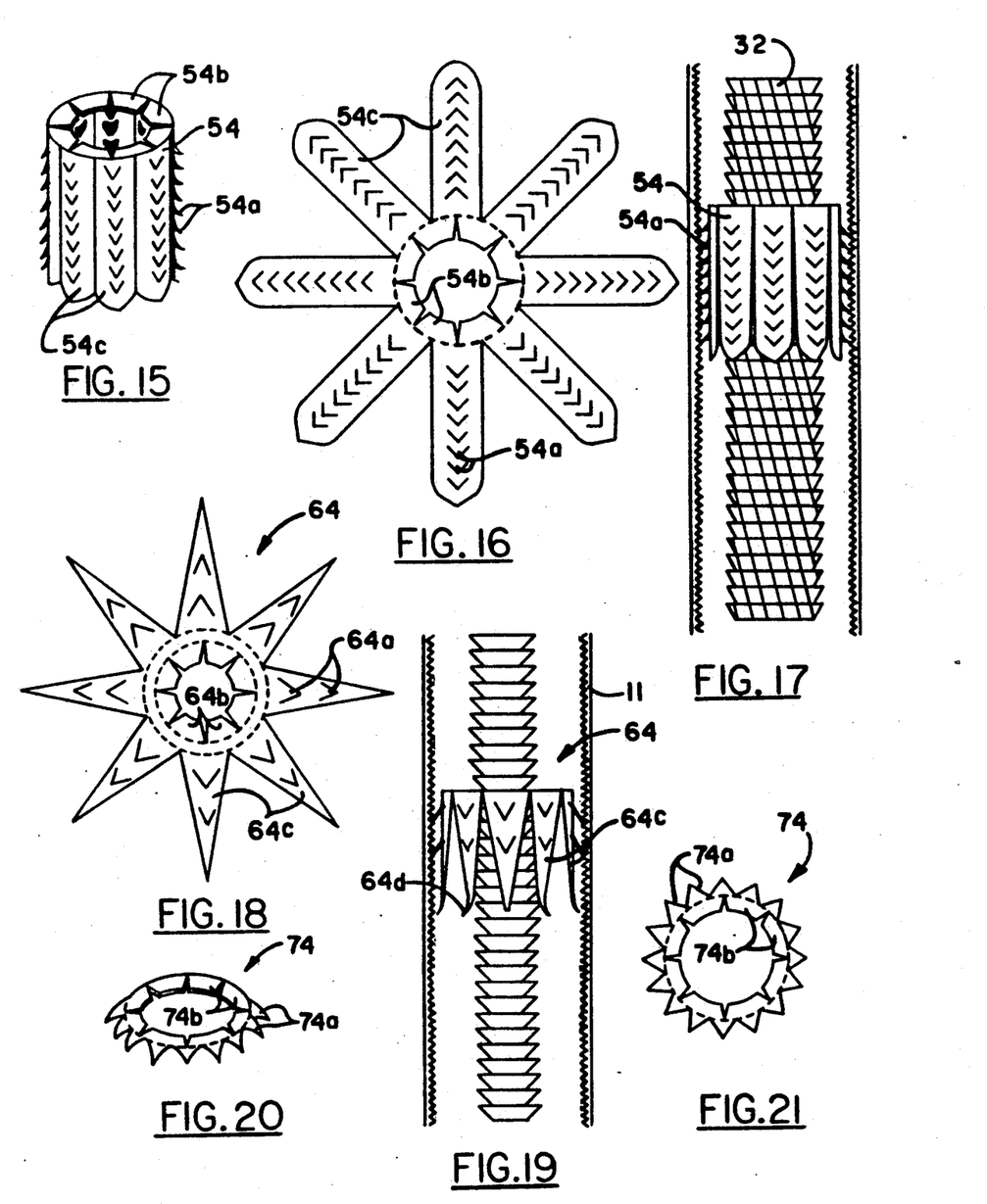
FIG. 15 shows a plunger lock stamped from sheet material.
FIG. 16 shows the stamping which yields the plunger lock of FIG. 15.
FIG. 17 shows a section of a syringe employing the plunger lock of FIG. 15.
FIG. 18 shows a stamping for another plunger lock.
FIG. 19 shows a section of a syringe employing the plunger lock produced from the stamping of FIG. 18.
FIGS. 20 and 21 show, respectively, pictorial and axial views of another plunger lock stamped from sheet material.

FIGS. 15–17 illustrate a plunger lock stamped from a resilient sheet material such as sheet metal. As best shown in FIG. 15, the leading end of plunger lock 54 is formed with inwardly and rearwardly struck tabs 54b. These engage the outer surface of plunger rod 32, as shown in FIG. 17, to form a one-way clutch. Folded back from the tabs so as to be longitudinally oriented are several arms 54c. Struck from the arms are several teeth 54a which, in the longitudinal orientation of the arms, extend rearwardly and outwardly. As shown in FIG. 17, the teeth engage the inner surface of syringe barrel 11 to form a one-way brake.

Another embodiment of a plunger lock stamped from resilient sheet material is illustrated in FIGS. 18 and 19. This plunger lock 64, like the plunger lock of FIGS. 15–17, has inwardly and rearwardly struck tabs 64b at its leading end and longitudinally extending folded back arms 64c with outwardly and rearwardly struck teeth 64a. However, the trailing ends of the arms are pointed to form an additional set of teeth 64d which engage the inner surface of the syringe barrel, as shown in FIG. 19, to form part of the one-way brake.

Another embodiment of a plunger lock stamped from sheet metal is shown in FIGS. 20 and 21. This plunger lock 74 is adapted for use in a syringe employing a relatively thick plunger rod with its outer surface located close to the inner surface of the barrel. The plunger lock has inwardly and rearwardly struck tabs 74b for engagement with the outer surface of the plunger rod and outwardly and rearwardly struck teeth 74a for engagement with the inner surface of the syringe barrel.

Figures 22, 23, 24, 25, 26:
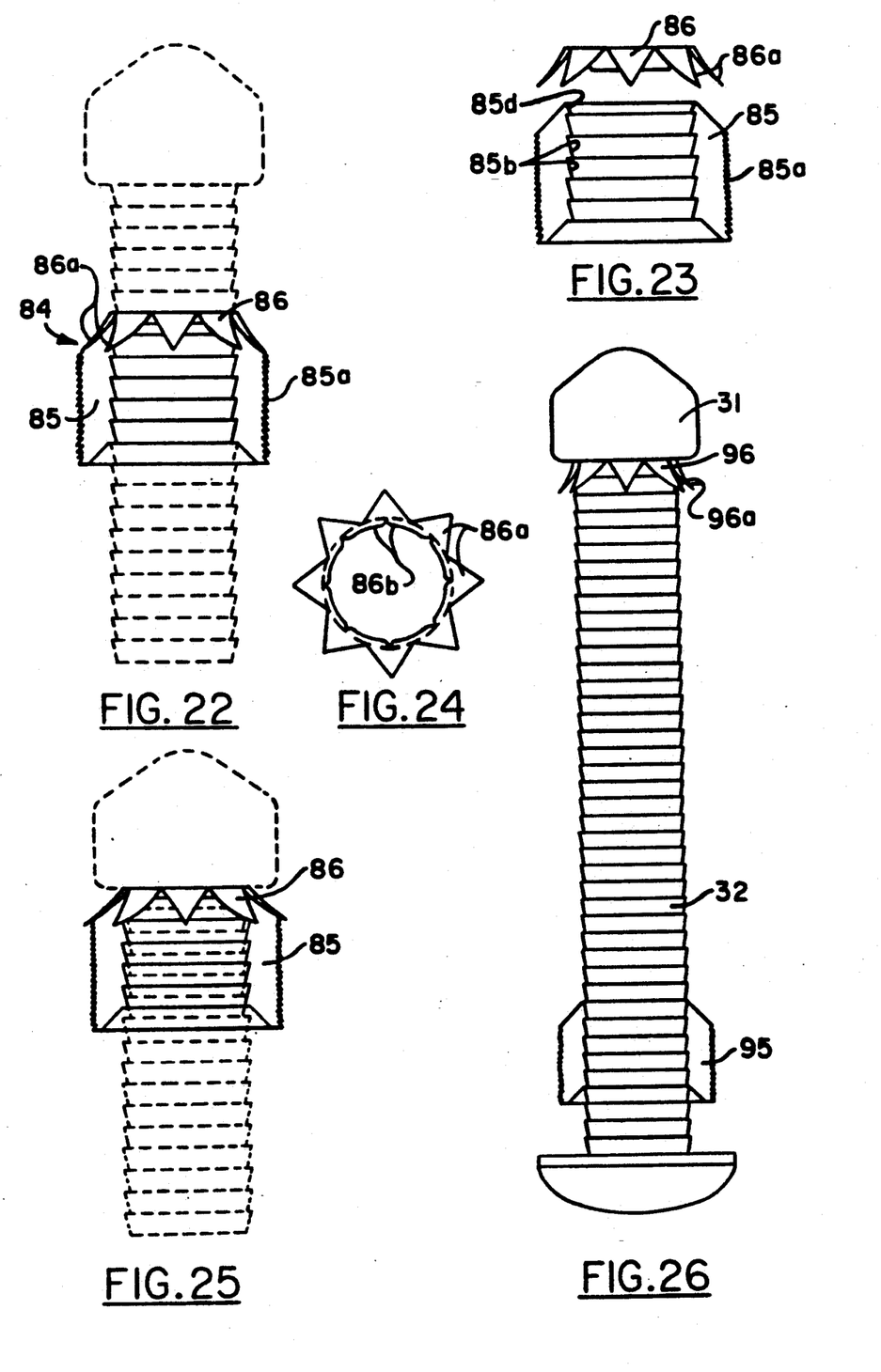
FIG. 22 shows a plunger assembly employing a double plunger lock with the spider teeth retracted.
FIG. 23 shows the assembly of the double plunger lock of FIG. 22.
FIG. 24 shows an axial view of the spider employed in the double plunger lock of FIG. 23.
FIG. 25 shows the plunger assembly of FIG. 22 with the spider teeth extended.
FIG. 26 shows a plunger assembly employing a double plunger lock with a spider located against a rearward face of the piston.

FIGS. 22–25 illustrate a double plunger lock 84 formed of two locking elements. As best shown in FIG. 23, the plunger lock includes an annular stopper 85 and a spider 86. The stopper is formed with rearwardly raked teeth 85a on its outer periphery and rearwardly raked teeth 85b on a surface defining a central opening through the stopper. Stopper 85 is thus similar to the plunger lock 24 shown in FIGS. 1–5: the teeth on the outer periphery engage corrugations on the inner surface of the syringe barrel to form a one-way brake, and the teeth about the central opening engage teeth formed on the outer surface of the plunger rod to form a one-way clutch. Spider 86 cooperates with the annular stopper to afford a particularly strong lock against rearward movement of the plunger lock in the syringe barrel. As best shown in FIGS. 23 and 24, the spider is stamped from sheet material and has inwardly and rearwardly struck central tabs 86b and outwardly and rearwardly struck peripheral teeth 86a. As shown in FIG. 22, the spider is positioned with teeth 86a, which are resilient and slightly curved, lying along the angled front face of the annular stopper. Tabs 86b lie along a forwardly facing side of the forwardmost inner tooth 85d (FIG. 23) in the stopper. As shown, tooth 85d does not intrude into the central opening of the stopper as much as the other teeth 85b, to thereby provide a clearance for accommodating the central tabs of the spider. In the unstressed condition of the spider, as shown in FIG. 22, the pointed ends of teeth 86a do not engage the inner wall of the syringe barrel. However, as shown in FIG. 25, when the piston in withdrawn into engagement with the spider, the force applied by the rear face of the piston to the spider causes the teeth 86a to ride outwardly along the angled front face of the stopper to effect engagement of the pointed ends of the teeth with the inner wall surface of the syringe barrel to supplement the one-way braking action of the interengaged teeth of the annular stopper and the inner surface of the barrel.

Figure 27:
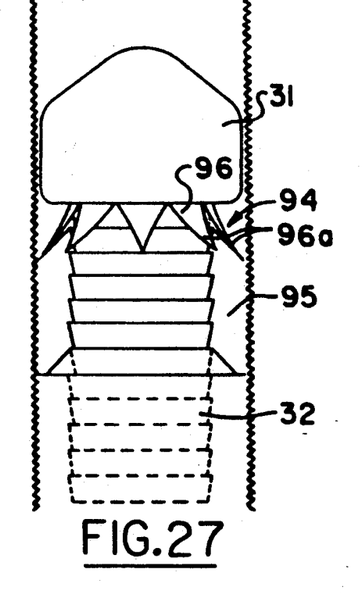
FIG. 27 shows a section of a syringe employing the plunger assembly of FIG. 26 with the spider teeth retracted.
Figure 28:
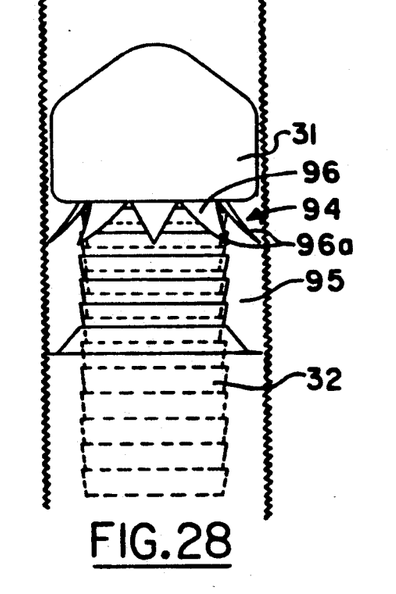
FIG. 28 shows a section of a syringe employing the plunger assembly of FIG. 26 with the spider teeth extended into engagement with the inner wall of the syringe barrel.
Figure 29:
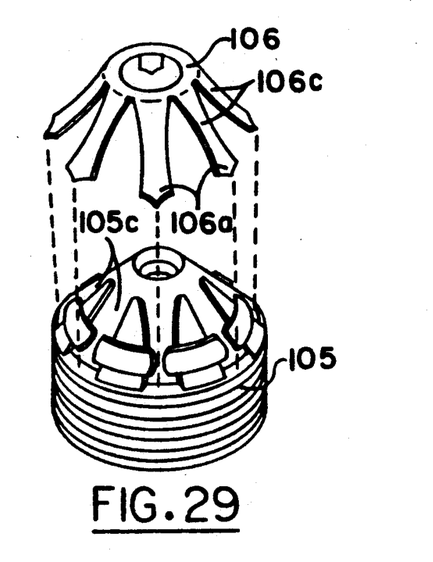
FIG. 29 shows the assembly of a double plunger lock in which the spider is carried on a forward face of the annular stopper.
Figure 30:
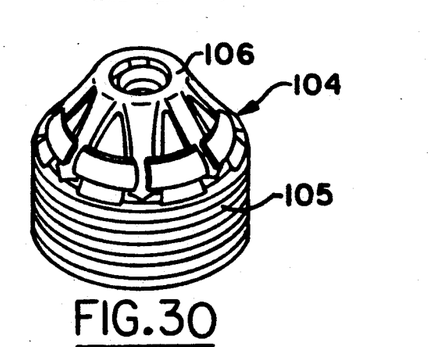
FIG. 30 shows the double plunger lock produced by the assembly of FIG. 29.

FIGS. 26-28 illustrate another embodiment of a double plunger lock 94 employs an annular stopper 95 and a spider 96. However, spider 96 is held between the forward end of plunger rod 32 and the rear face of piston 31. The operation is similar to that of the embodiment of FIGS. 22-25: rearward movement of the piston and plunger rod will bring the teeth 96a of the spider into engagement with the angled front face of the annular stopper; the teeth 96a will ride outwardly along the front face of the stopper into engagement with the inner wall of the syringe barrel.

Figures 31, 32, 34, 35, 36:
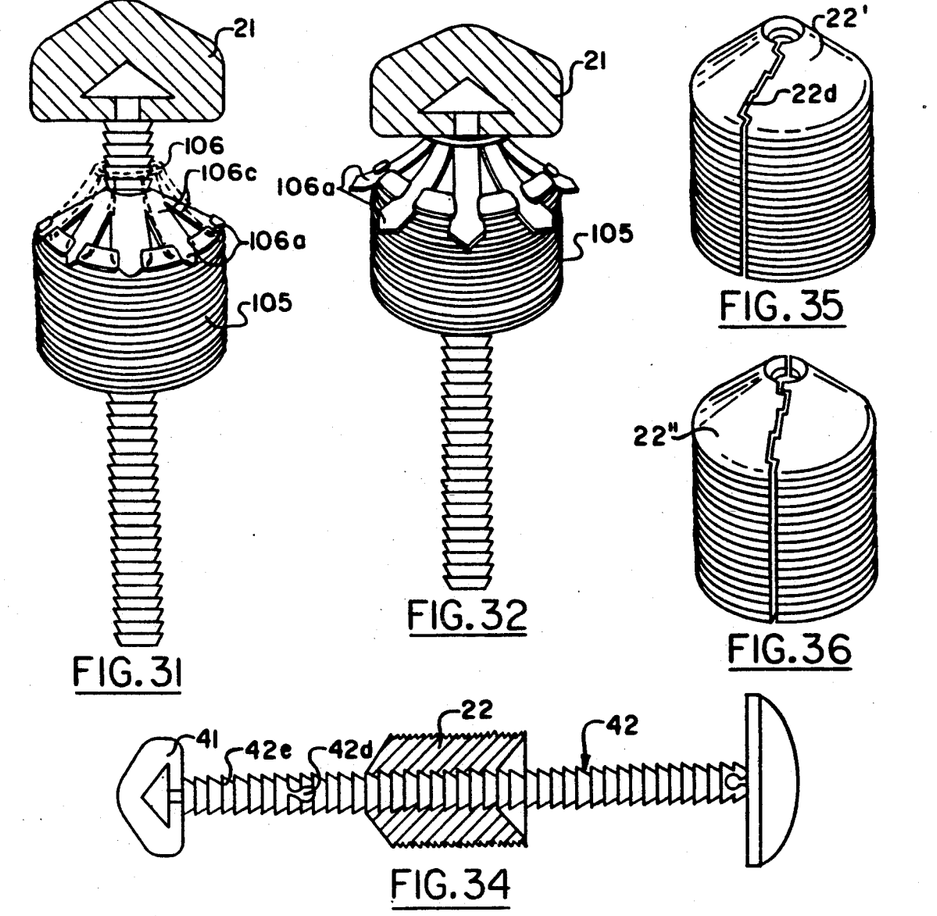
FIG. 31 shows a plunger assembly employing the double plunger lock of FIG. 30 with the spider teeth retracted.
FIG. 32 shows the plunger assembly of FIG. 31 with the spider teeth extended.
FIG. 34 shows a plunger assembly employing a segmented plunger rod.
FIG. 35 shows a plunger lock in the form of an annular stopper which is split along one side.
FIG. 36 shows a plunger lock in the form of an annular stopper which is formed of mating halves.
Figure 33:
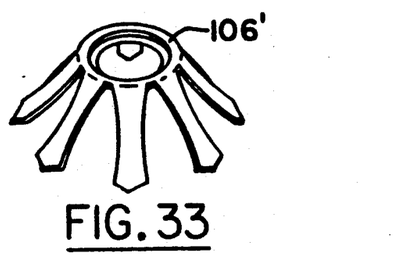
FIG. 33 shows a modification of the spider employed in the double plunger lock of FIG. 30.

FIGS. 29-33 illustrate the construction and operation of another embodiment of a double plunger lock. Like the plunger locks shown in FIGS. 22-25 and 26-28, plunger lock 104 incorporates an annular stopper 105 and a spider 106. The is formed with radiating channels 105c in its angled front face which slidably retain the resilient arms 106c of the spider. As shown in FIG. 31, when the spider 104 is spaced from piston 21, the pointed ends 106a of arms 106c are withdrawn from engagement with the inner wall of the syringe barrel. However, as shown in FIG. 32, when the piston is withdrawn into engagement with the spider, the arms of the spider ride outwardly in the channels 105c of the annular stopper to place the pointed ends 106a into engagement with the inner wall of the syringe barrel to supplement the rearward braking effect of the annular stopper against the inner wall of the syringe. The surface of the spider surrounding its central opening may be either flat, as in the spider 106 shown in FIG. 29, or indented, as in the spider 106' shown in FIG. 33.

FIG. 34 shows a plunger assembly which employs a segmented plunger rod 42 which could be used in any of the embodiments of the invention. At its forwardmost end the plunger rod is strongly joined to piston 41. The plunger rod has an intermediate joint 42d located rearwardly of the piston at a distance approximately equal to the axial extent of the central opening of the plunger lock 22. If the piston is pulled rearwardly against the plunger lock with sufficient force, joint 42d will separate leaving a short forward segment 44e of the plunger rod within the opening of the plunger lock to thus block access to the forward end of the plunger lock and deter manipulation of the plunger lock by tools inserted through the rear end of the barrel.

FIGS. 35 and 36 illustrate two constructions of a plunger lock or annular stopper used, for example, in the embodiments of FIG. 1 and FIG. 22. As shown in FIG. 35, the plunger lock 22' is split at joint 22d along one side. The plunger lock is formed of material with a resiliency which permits forcing the mating surfaces of the joint apart for assembly of the plunger lock to the plunger rod. Alternatively, a gap could be provided along one side of the plunger lock to permit insertion of the plunger rod. The plunger lock 22" shown in FIG. 36 is formed of two mating halves which may be joined by an integral hinge at the exterior peripheral surface of the plunger lock along one side thereof. This two-piece construction is easy to manufacture and assemble to the plunger rod. The plunger locks shown in FIGS. 35 and 36 are shown with rearwardly raked teeth 22a extending entirely about their perpheries. This configuration is not essential, however, and longitudinally extending rows of annular tooth segments separated by smooth peripheral surface segments would also provide the desired one-way braking against the inner surface of the syringe barrel.

Figure 37:
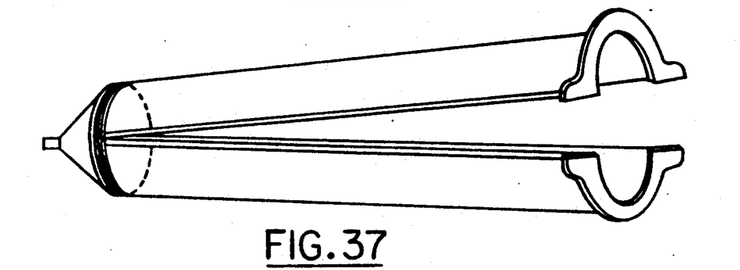
FIG. 37 shows a syringe barrel formed of flexibly joined mating barrel halves.

FIG. 37 illustrates a construction for a plastic syringe barrel 11' which is formed of two barrel halves 11b, 11c joined together at their forward ends. A flexible semi-annular segment at the forward end of each barrel half allows the rear ends of the barrel halves to move apart to facilitate removal of the barrel from a mold and insertion of the plunger assembly. After the plunger assembly is inserted, the barrel halves can be sealed together using, for example, conventional welding techniques. An inwardly extending lip 11d at the rear end of the barrel acts as a retainer for the plunger assembly.

Variations or modifications of the above-described invention which would be obvious to persons of ordinary skill in the art are to be regarded as falling within the scope of the invention as defined in the following claims.

I claim:

1. A restricted use hypodermic syringe comprising:
   a tubular barrel having a forward end, a rearward end and an inner wall surface defining an interior space for accommodating a liquid to be administered and a movable plunger assembly, said barrel having means at said forward end thereof for coupling to a hypodermic needle;
   a movable plunger assembly received within said barrel, said plunger assembly having (1) a piston with an exterior surface sealingly engaging said inner wall surface of said barrel, (2) a plunger rod having a forward end joined to said piston and a rearward end extending through said rearward end of said barrel and (3) a plunger lock disposed between and engaging said plunger rod and said inner wall surface;
   said plunger rod and said plunger lock having interengaging surfaces forming a one-way clutch which permits movement of said piston and plunger rod relative to said plunger lock in a rearward direction and couples said piston and plunger rod and said plunger lock for movement together in a forward direction;
   said plunger lock having surfaces engaging the inner wall of said barrel to form a one-way brake which permits movement of said plunger lock in said barrel in a forward direction and prevents movement of the plunger lock in a rearward direction;
   whereby (1) the piston and plunger rod can be moved rearwardly in said barrel from a first position to a second position for drawing liquid into said barrel, (2) subsequently said piston and plunger rod and said plunger lock can be moved together in said barrel forwardly from said second position to a third position to expel liquid from said interior space and establish a blocking position of said plunger lock and (3) thereafter the extent of rearward movement of said piston and plunger rod in said barrel is limited by the blocking position of said plunger lock.

2. The restricted use hypodermic syringe of claim 1 wherein annular corrugations are provided on said inner wall of said barrel.

3. The restricted use hypodermic syringe of claim 2 wherein said plunger lock comprises an annular stopper with rearwardly raked teeth engaging said annular corrugations to form said one-way brake.

4. The restricted use hypodermic syringe of claim 2 wherein said corrugations are in the form of forwardly raked annular ridges.

5. The restricted use hypodermic syringe of claim 3 wherein said annular stopper carries rearwardly raked teeth on the surface of a central opening through said annular stopper, and said plunger rod carries forwardly raked teeth, said rearwardly raked teeth on said annular stopper and said forwardly raked teeth on said plunger rod interengaging to form said one-way clutch.

6. The restricted use hypodermic syringe of claim 3 wherein said plunger lock further comprises a spider positioned about said plunger rod between said piston and said annular stopper.

7. The restricted use hypodermic syringe of claim 6 wherein said annular stopper has an outwardly and rearwardly angled forward face, and said spider carries outwardly and rearwardly angled teeth normally out of engagement with said annular corrugations, said teeth being deflectable into engagement with said annular corrugations when rearward movement of said piston causes said teeth to slide outwardly along said forward face of said annular stopper.

8. The restricted use hypodermic syringe of claim 7 wherein said spider is carried on said forward face of said annular stopper.

9. The restricted use hypodermic syringe of claim 7 wherein said spider is carried on said plunger rod in engagement with said piston.

10. The restricted use hypodermic syringe of claim 1 wherein said plunger lock comprises a tubular element of resilient material surrounding said plunger rod.

11. The restricted use hypodermic syringe of claim 10 wherein said tubular element carries (1) outwardly and rearwardly angled teeth engaging said inner wall surface of said barrel to form said one-way brake and (2) inwardly and rearwardly angled tabs engaging said plunger rod to form said one-way clutch.

12. The restricted use hypodermic syringe of claim 11 wherein said teeth are provided at forward and rearward ends of said tubular element.

13. The restricted use hypodermic syringe of claim 11 wherein said tubular element further comprises arms which are longitudinally oriented in said barrel, and said teeth are struck from said arms.

14. The restricted use hypodermic syringe of claim 1 wherein said plunger lock comprises a stamped element of resilient material surrounding said plunger rod.

15. The restricted use hypodermic syringe of claim 14 wherein said stamped element carries (1) outwardly and rearwardly angled teeth engaging said inner wall surface of said barrel to form said one-way brake and (2) inwardly and rearwardly angled tabs engaging said plunger rod to form said one-way clutch.

16. The restricted use hypodermic syringe of claim 15 wherein said stamped element further comprises arms which are longitudinally oriented in said barrel, and said teeth are struck from said arms.

* * * * *